United States Patent
Smith

(10) Patent No.: US 8,287,519 B2
(45) Date of Patent: Oct. 16, 2012

(54) SELF-CLEANSING BLADDER DRAINAGE CATHETER

(75) Inventor: David Smith, Richmond, IN (US)

(73) Assignee: Smith Tech Innovations, LLC, Richmond, IN (US)

( * ) Notice: Subject to any disclaimer, the term of this patent is extended or adjusted under 35 U.S.C. 154(b) by 1531 days.

(21) Appl. No.: 11/553,780

(22) Filed: Oct. 27, 2006

(65) Prior Publication Data

US 2008/0172040 A1    Jul. 17, 2008

(51) Int. Cl.
*A61M 27/00*    (2006.01)

(52) U.S. Cl. .................. 604/544; 604/19; 604/540

(58) Field of Classification Search ......... 604/95.01, 604/95.02, 95.03, 95.04, 95.05, 275, 276, 604/277, 278, 523, 524, 525, 526, 174, 175, 604/176, 177, 178, 179, 180, 540, 317, 327, 604/328, 346, 347, 348, 349, 353, 350, 351, 604/352, 544, 527, 528, 529, 530, 531, 532, 604/104, 105
See application file for complete search history.

(56) References Cited

U.S. PATENT DOCUMENTS

| | | | |
|---|---|---|---|
| 1,120,549 A * | 12/1914 | Schellberg | 604/171 |
| 1,661,494 A * | 3/1928 | Nielsen | 604/174 |
| 2,450,217 A | 9/1948 | Alcorn | |
| 3,260,258 A | 7/1966 | Berman | |
| 3,769,981 A | 11/1973 | McWhorter | |
| 3,811,450 A | 5/1974 | Lord | |
| 3,815,608 A | 6/1974 | Spinosa et al. | |
| 3,898,993 A * | 8/1975 | Taniguchi | 604/172 |
| 4,307,723 A | 12/1981 | Finney | |
| 4,419,097 A * | 12/1983 | Rowland | 604/174 |
| 4,501,580 A | 2/1985 | Glassman | |
| 4,643,720 A | 2/1987 | Lanciano | |
| 4,645,493 A | 2/1987 | Ferrando et al. | |
| 4,710,169 A * | 12/1987 | Christopher | 604/104 |
| 4,723,946 A | 2/1988 | Kay | |
| 4,738,667 A | 4/1988 | Galloway | |
| 4,740,195 A | 4/1988 | Lanciano | |
| 4,810,247 A * | 3/1989 | Glassman | 604/171 |
| 5,007,897 A * | 4/1991 | Kalb et al. | 604/43 |
| 5,049,140 A | 9/1991 | Brenner et al. | |
| 5,141,502 A | 8/1992 | Macaluso, Jr. | |
| 5,176,664 A | 1/1993 | Weisman | |
| 5,246,445 A | 9/1993 | Yachia et al. | |
| 5,282,784 A | 2/1994 | Willard | |
| 5,306,226 A * | 4/1994 | Salama | 600/29 |
| 5,523,092 A | 6/1996 | Hanson et al. | |

(Continued)

OTHER PUBLICATIONS

Preliminary Search Report with Written Opinion for corresponding PCT US2007/082542, Apr. 10, 2008.

*Primary Examiner* — Tatyana Zalukaeva
*Assistant Examiner* — Benedict L Hanrahan
(74) *Attorney, Agent, or Firm* — Maginot, Moore & Beck, LLP

(57) ABSTRACT

An indwelling endourethral drainage catheter includes a tubular distal portion and a spiral proximal portion. A central lumen extends along substantially the entire length of the catheter. The spiral proximal portion defines an outer spiral channel in fluid communication with the central lumen. The distal end of the catheter is anchored externally so that the catheter is held against advancement into or out of the urethra. In certain methods, the diameter of the spiral proximal portion may be changed to address obstructions within the urethra or facilitate navigation of the catheter along the urethra.

8 Claims, 3 Drawing Sheets

U.S. PATENT DOCUMENTS

| | | | |
|---|---|---|---|
| 5,658,264 A * | 8/1997 | Samson | 604/526 |
| 5,795,334 A | 8/1998 | Cochrane, III | |
| 7,171,275 B2 * | 1/2007 | Hata et al. | 607/122 |
| 2005/0251108 A1 * | 11/2005 | Frassica | 604/540 |
| 2005/0267442 A1 * | 12/2005 | Von Oepen | 604/509 |
| 2007/0233043 A1 * | 10/2007 | Dayton et al. | 604/526 |

* cited by examiner

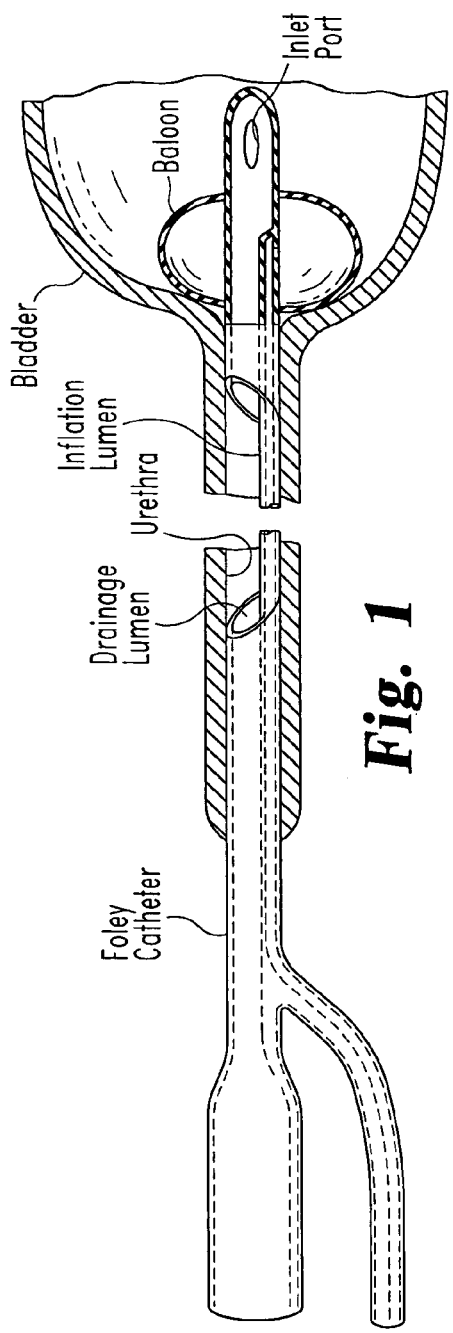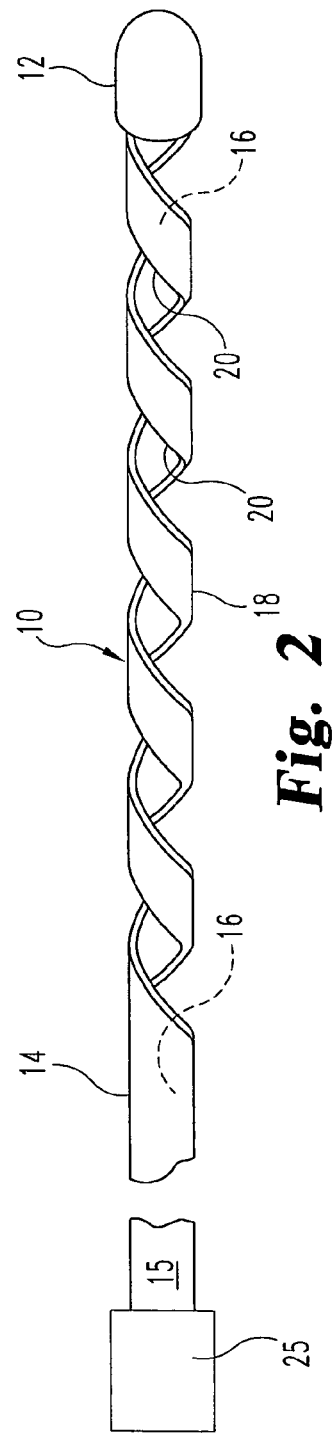

SELF-CLEANSING BLADDER DRAINAGE CATHETER

BACKGROUND

The present invention relates to a catheter for disposition within the urinary tract of a patient. More particularly, the invention concerns an indwelling drainage catheter.

The urinary tract of a patient includes the kidneys, ureters, bladder, urethra and, in men, the prostate which encircles the urethra adjacent the bladder. The bladder consists of the body, the trigone and the bladder neck. In the male, the urethra is typically divided into three sections—the prostatic, extending along about the upper 4 cm of the urethra; the membranous section, which narrows from the prostatic for about 1 cm; and the cavernous which continues to the glans for about 15 cm. The lumen of the urethra has a number of deep, irregular outpocketings, a multitude of glands, and a rich network of capillaries.

Problems in the urinary tract can have serious consequences, particularly when the problem is one of retention or incomplete emptying. Retention problems can result from any of a number of causes, including without limitation, spinal cord injury, typhoid, peritonitis, prostatic enlargement, urethral stricture, urethritis, cystitis, bladder tumors, or urethral calculus. Patients suffering from these and other conditions often require some interventional means to periodically drain or augment drainage of the bladder. Further, the clinician often requires indwelling urinary drainage to monitor urine production more closely, especially post-operatively. Failure to do so can result in damage of the epithelium and detrusor muscles associated with the bladder, and an increased potential for bacterial invasion which is commonly thought to contribute to urinary tract infection potentially leading to life-threatening urosepsis or kidney failure.

These urinary tract problems may manifest themselves with a variety of symptoms, such as: (i) incomplete emptying, (i.e., the patient is only able to urinate small volumes, e.g. <100 milliliters (ml), or has an elevated volume of urine left in the bladder following urination, e.g. >100 ml per attempt); (ii) experiencing frequent urges to urinate; (iii) intermittency (e.g. a patient's flow stops and starts often during urination); (iv) having a very weak and inconsistent urine flow stream; and (v) stress incontinence (e.g. leaking during lifting or straining as a result of excessive urine in the bladder or weakened sphincters).

Up to two million office visits annually in the United States are attributed to patients being bothered by some form of lower urinary tract symptoms (LUTS). For men, the symptoms are typically suspected to be caused by the intrusion of an enlarged prostate gland upon the urethra. Bladder outlet obstructions (BOO) are a major subgroup of LUTS. It is estimated that nearly 75% of men between the ages of 55 and 75 years have some degree of bladder outlet obstruction. Bladder outlet obstructions are primarily caused by the enlargement of the prostate gland (e.g., benign prostate hyperplasia (BHP)) which results in radial compression of the urethra surrounded thereby (i.e., the prostatic urethra), thus obstructing (i.e., constricting) urine flow, resulting in incomplete emptying of the bladder (i.e., there being what is clinically referred to as a "post void residual" (PVR) remaining in the bladder).

Devices have been developed to be positioned in the urethra and/or bladder to correct the problems of obstruction and incontinence of urine flow. Heretofore known problems associated with endourethral devices, more particularly critical device components such as stents, valve actuators, flow conduits, etc., generally relate to the physiology of the lower urinary tract (e.g., ingrowth, instability, pitting, depositions, etc.). Problems of device leakage or less than complete emptying of the bladder are widely encountered. Furthermore, issues surrounding device deployment and fit, positioning, repositioning, and retention (i.e., sufficient anchoring) have been well documented. Catheter associated urinary tract infections (CAUTI's) are frequently the result of legacy indwelling drainage devices and it is thought that up to 100,000 deaths/year can be attributed these devices.

It is especially critical that the endourethral device be stable with respect to position (i.e., deployed in a physiologically properly and stable position), and comfortable to wear, as the urinary tract is sensitive to contact and friction. Interurethral stents have been utilized within the prostatic region, although many users foregoing such devices for alternate therapies due to feelings of discomfort and/or pain. Many endourethral devices have similarly been evaluated for urinary incontinence for females. Based upon clinical findings, many have been shown to be uncomfortable, thus severely retarding their utility as a therapy. Other devices have migrated into the bladder, or have been expelled under straining conditions.

One common drainage catheter is the Foley catheter and variations thereof. The traditional Foley catheter includes an inflatable balloon at the distal end of a catheter tube, as depicted in FIG. 1. The balloon is deflated as the tube is advanced up the urethra toward the bladder. Once the balloon traverses the bladder sphincter, the balloon is inflated to prevent only anterograde movement of the catheter within the urethra. The proximal end incorporates a drainage inlet port in communication with the catheter lumen for draining urine from the bladder. The distal end also includes an inflation lumen that is adapted to engage a source of saline for inflating the balloon in situ. The distal end protrudes beyond the urethral orifice and can be attached to a receptacle for collection of the nearly constantly dripping urine. Optionally, a plug or valve may be incorporated at the distal end to stop the flow of urine. While the traditional Foley catheter uses a balloon for retention, variations have incorporated alternative elements that are expandable and contractible within the bladder. These variations all require an additional lumen for passage of a control component for controlling the expansion or contraction of the alternative element within the bladder.

One problem associated with the Foley-type catheter is that the retention balloon or element rests against the dome of the bladder an area thought to be only three cells thick. Placement of a retention device in this region often leads to pooling of urine, or dead space, and may be partially responsible for the multitude of infections caused by this device. This aspect can also cause tissue compression and irritation of the sensitive tissue lining the bladder, sometimes leading to erosion of the tissue. The pressure of the retention element may also aggravate the micturition reflex, or the electrical signal to urinate. The bladder contracts in response to this signal, which leads to further pressure and irritation at the area of contact between the bladder and the retention element. These bladder contractions can further result in oscillation of the catheter proximally and distally since there is no anchoring the catheter to prevent movement in the proximal direction. In some cases, inadequate deflation or retraction of the retention element can occur, leading to extreme discomfort and even damage to the urethra upon withdrawal. The presence of the additional lumen for introduction of inflation fluid or other actuation feature for the catheter dramatically reduces the flow area of the drainage lumen.

Another problem associated with the Foley-type drainage catheter is that the balloon or other retention element only prevents retrograde movement, or movement distally toward the urethral orifice. The retention element does not prevent movement of the retention element and catheter deeper into the bladder. Obviously, excessive distal movement of the catheter may cause physical damage to the bladder. Irritation or abrading of the mucosa within the urethra may also result by the continuous sliding back and forth of the catheter within the urethra.

However, a more insidious result of this distal movement is the increased instance of urinary tract infections. It has been suggested that the increase in infection rate for long indwelling catheter patients is due to migration of bacteria up the urethra, coined "biofilm creep." In particular, it is believed that bacteria infecting the distal end of the drainage catheter can be carried into the urethra by each proximal movement of the catheter. As the bacteria are advanced upward by this proximal movement, they adhere to the tissue of the urethra. Some of the bacteria hold their position as the catheter resets distally, only to hitch a ride again when the catheter again moves proximally toward the bladder. It has been suggested that this biofilm creep mechanism allows bacteria to travel from the urethral orifice to the bladder in a matter of minutes. Urine that would otherwise help "flush" the urethra is isolated from the urethra as it passes through the drainage lumen of the Foley catheter.

It is expected that an increasing number of long-term drainage catheterizations will occur, especially as patients live longer. Conventional drainage catheters are not designed for prevent expensive and life threatening infections. There is a significant need for a urinary drainage catheter that avoids these problems associated with the Foley-type catheter.

SUMMARY OF THE INVENTION

In order to address this need for an improved indwelling endourethral drainage catheter the present invention contemplates a drainage catheter comprising a tubular distal portion having a distal end adapted to be situated outside the patient when the drainage catheter is indwelling and a spiral proximal portion attached to said distal portion. A central lumen extends through the proximal and distal portions for drainage of urine therethrough. In accordance with one feature of the invention, the proximal portion defines a helical outer channel along the length thereof with the outer channel in fluid communication with the central lumen. In a specific embodiment, the proximal and distal portions are integrally formed and the proximal portion is provided with a tip configured for smooth insertion into the urethra and bladder. A fluid fitting is provided at the distal end for connection of the drainage catheter to a receptacle, urine monitoring device or other suitable component.

The drainage catheter further comprises an anchor assembly for anchoring the catheter within the urethra. In one aspect of the invention, the anchor assembly is disposed entirely externally of the bladder and urethra and is configured to maintain the helical outer in communication with the bladder. In one embodiment, the anchor assembly includes a shroud configured to be disposed over the opening of the urethra of the patient and an engagement between the shroud and the distal portion of the catheter outside the urethra. In certain embodiments, this engagement includes a friction engagement between the shroud and the outer surface of the distal portion outside the urethra, as may be achieved by forming the shroud and distal portion of like material. In an alternative embodiment, the engagement includes a clamping element encircling the shroud mounted on an outer surface of the distal portion outside the urethra. This clamping element may be in the form of an O-ring or encircling strap. In yet another embodiment, the anchor assembly may include an adhesive strip disposed between the patient's skin and the shroud when the shroud is disposed over the opening of the urethra.

In another aspect of the invention, an indwelling endourethral drainage catheter is provided that comprises a tubular body having a proximal end with a blunt tip configured to pass freely through the urethra into the bladder, a distal end extending from the proximal end to outside the urethra when the catheter is indwelling, and a central lumen passing substantially entirely therethrough. In this aspect, the drainage catheter further comprises only an external anchor assembly, disposed outside the bladder and urethra, which is configured to anchor the tubular body within the urethra with the blunt tip within the bladder. Thus, in this embodiment, no internal anchor, such as a Foley-type anchor, is employed to maintain the position of the drainage catheter within the urethra.

The present invention further contemplates a method for advancing an indwelling endourethral drainage catheter along the urethra of a patient into the bladder that comprises providing a drainage catheter having at least a spiral proximal portion and a distal portion, and rotating the proximal portion relative to said distal portion so that the diameter of the proximal portion changes. It is contemplated that rotating the proximal portion in one direction reduces the outer diameter, while rotation in the opposite direction increases the outer diameter. The reduced diameter state may be advantageous for advancing the catheter along the urethra. The larger diameter state of the proximal portion may be advantageous to bear against an obstruction within the urethra.

In yet another method of the invention, a drainage catheter is provided having a spiral proximal portion and a tubular distal portion, the catheter defining a central lumen therethrough and the proximal portion defining an outer channel in fluid communication with the central lumen. The drainage catheter is advanced into the urethra until an obstruction is encountered. At this point, the present invention contemplates rotating the distal portion to engage the obstruction within the outer channel. Further rotation of the distal portion may be used to advance the obstruction along the outer channel into the central lumen. Alternatively, further rotation of the distal portion may be used to advance the obstruction along the outer channel toward and into the bladder.

It is one object to provide an indwelling ureteral drainage catheter that avoids the biofilm creep problems associated with prior drainage catheters. Another object is to provide a drainage catheter that may be very easily and simply anchored to the patient.

One significant benefit of the drainage catheter of the present invention is that it is easy to deploy while still providing a stable anchorage within the urethra. A further benefit is that the catheter provides unique mechanisms for negotiating the urethra and obstructions that may be encountered as the catheter is advanced into the bladder. Other objects and benefits of the invention will become apparent upon consideration of the following written description and the accompanying figures.

DESCRIPTION OF THE FIGURES

FIG. 1 is a side partial cross-sectional view of a Foley-type endourethral catheter in situ.

FIG. 2 is a side view of an endourethral catheter in accordance with one embodiment of the present invention.

DESCRIPTION OF THE EMBODIMENTS

Figure 3:
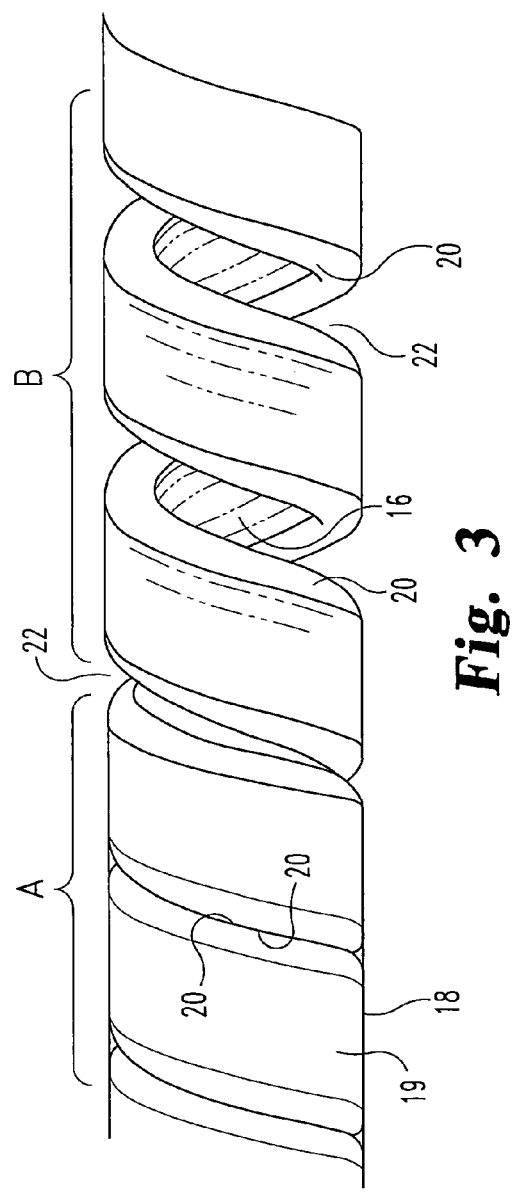
FIG. 3 is an enlarged view of a proximal portion of the catheter shown in FIG. 2 shown in a one state.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates an indwelling urinary drainage catheter 10 shown in FIG. 2 that includes a proximal tip 12 sized and configured to pass through the bladder sphincter into the bladder. The proximal tip 12 is preferably bullet-nosed or rounded to facilitate passage through the urethra and to minimize the potential for damage to the delicate tissues within the urethra. As shown in FIG. 2, the proximal tip does not incorporate any retention element, such as the balloon tip of the typical Foley catheter. Although some form of retention element may be included in the proximal tip 12, the present invention contemplates anchoring of the catheter 10 outside the patient's body, as explained in more detail herein. In addition, the tip may be provided with openings for fluid flow, although the present invention does not require openings of this sort. This proximal tip may be radio-opaque for visibility by x-ray or other imaging source to verify the position of the tip. In a specific embodiment, the proximal tip 12 may have a length of about 6 mm.

The catheter 10 includes a distal tubular portion 14 that terminates in a fitting 25 configured for attachment to a drainage container. It can first be appreciated that the catheter 10 has a length from the proximal tip 12 to the fitting 25 that is sufficient to at least span the length of the urinary tract from the inside of the bladder adjacent the bladder sphincter to beyond the urethral orifice. Preferably, the length of the catheter is such that the fitting 25 is situated sufficiently beyond the end of the urethra to readily accessible by medical personnel, such as for connecting the catheter to a suitable container for receiving urine drained through the catheter. In addition, the length of the catheter is sized so that a suitable length of the distal tubular portion 14 is exposed beyond the end of the urethra to provide a site for anchoring the catheter. In one embodiment, the catheter is provided in a single length that is known to accommodate all patient anatomies. In this embodiment, the catheter has a length of about 40 cm (16 inches). In an alternative embodiment, it is contemplated that the catheter 10 may be provided in several discrete lengths, with an appropriately sized catheter selected based on the patient's gender and anatomy. The proximal tubular portion 14 preferably constitutes the majority of the catheter, so the length of that portion measured from the fitting 25 may be about 30 cm. It is contemplated that the entire tubular catheter may contain a radio-opaque coating or strip that will make it readily visible through external imaging.

The diameter of the distal tubular portion 14 is also sized based on standard anatomical dimensions for the urethra. It is important that the tubular portion 14 fit snugly, but not tightly, within the urethra. Thus, it is contemplated that the catheter 10 may be provided in several diameters, preferably ranging from 12 French to 30 French in 2 French increments. Thus, the outer diameters for the selection of catheters preferably range from 4 mm to 11 mm.

The distal tubular portion 14 defines an inner lumen 16 for flow of urine through the catheter. The inner diameter of the lumen 16 must be sufficient for adequate flow. It is therefore contemplated that the lumen 16 has an inner diameter of at least 3 mm. In one embodiment, the lumen diameter may be the same regardless of the outer diameter dimension of the tubular portion. However, since the catheter 10 must have sufficient flexibility to navigate turns during insertion into the urethra, the tubular wall thickness is important. Thus, in the preferred embodiment, the wall thickness of the distal tubular portion 14 is maintained generally constant regardless of outer diameter dimension. It is contemplated in one specific embodiment that catheter 10 is formed of a medical grade polymer, such as Krayton. In other embodiments the catheter may be formed of latex or silicone and may incorporate hydrogel or antibiotic impregnations. For this material, it is believed that a wall thickness of 0.5 mm provides an acceptable degree of flexibility to navigate turns, while retaining sufficient stiffness to avoid buckling as the catheter is pushed up the urethra. It is known that the wall of the urethra itself exerts an inward force that helps maintain the patency of the catheter 10 as it is advanced distally. Thus, a thinner wall thickness may be acceptable in alternative embodiments.

In accordance with one feature of the invention, the proximal portion 18 of the drainage catheter 10 constitutes a wound or spiral tube, as illustrated in FIG. 2. The central lumen 16 passes through the spiral distal portion 18 to provide an unobstructed flow path for urine. An additional flow path is provided between the opposite edges 20 of the spiral tube. Thus, as shown in FIG. 3, an outer channel 22 is defined between the inner lumen 16 and the outer circumference of the proximal portion 18. This outer channel 22 provides several beneficial features to the catheter. First, the outer channel communicates directly with the bulb or base of the bladder where urine collects at the bladder sphincter. In prior Foley-type catheters (often having only two drain islets), the urine pools at this location, rather than fully draining from the bladder. Any urine that leaks past the anchor balloon of the Foley catheter bypasses the catheter lumen, which can result in an embarrassing leakage problem for the patient. As explained further below, the catheter 10 of the present invention is anchored to the patient so that the proximal tip 12 is offset from the bladder sphincter so that the outer channel 22 is always in fluid communication with the bladder, even at the typical pooling location.

A second feature of the spiral proximal portion 18 is that the outer channel creates a vortex effect as urine drains through that the channel and enters the inner lumen 16. This vortexing of the fluid helps hold the urethra open and overcomes surface tension of fluids pooled in dead spaces in the bladder or urethra. Vortexing fluids better maintain equalized pressures proximally and distally providing for optimal forward flow. Moreover, this vortex flow helps clean the wall of the urethra open to the channel, thereby retaining the ability to flush contagion or bacteria as through normal urination.

Figure 4:
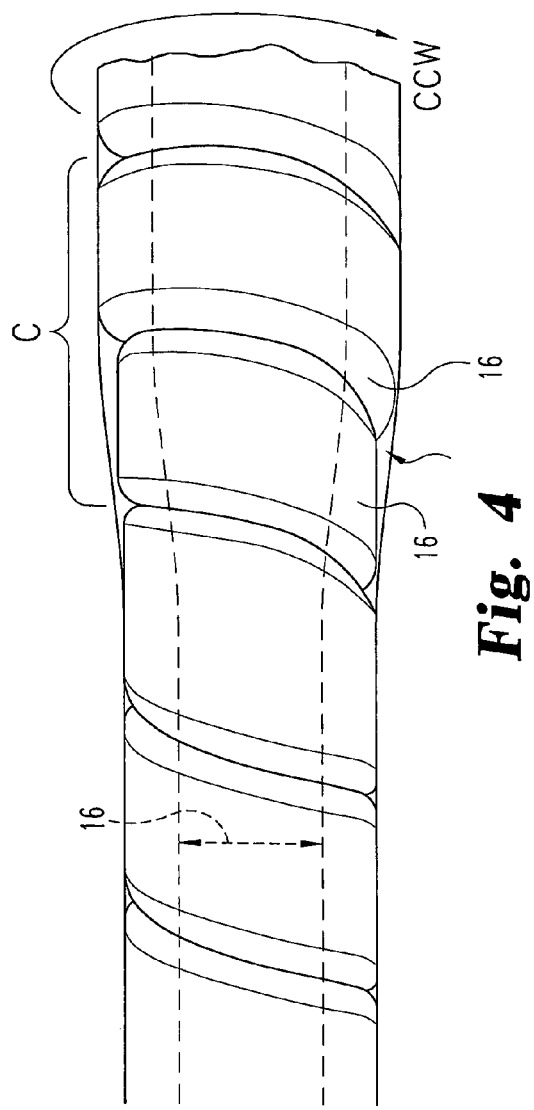
FIG. 4 is an enlarged view of the proximal portion depicted in FIG. 3, shown in another second state.

A third feature provided by the spiral proximal portion 18 is the ability to achieve multiple states, as seen by comparing the views of FIGS. 3 and 4. As shown in FIG. 3, the spiral proximal portion 18 may have a first state A in which the coil is tightly wound with the edges 20 effectively in contact with each other. This is accomplished by the operator using a continuous gentle rotational force in a clockwise manner while inserting, similar to using a screwdriver to screw in a screw. This state A may occur as the catheter is maneuvered up the urethra and into the bladder to improve the axial rigidity of the catheter.

Once the proximal tip 12 is properly located inside the bladder sphincter, the spiral proximal portion 18 may be expanded to the second state B, also shown in FIG. 3. This secondary state may be accomplished by reversing the gentle rotational force to the counter-clockwise direction. In this state, the circumferential channels 22 are opened between the edges 20 and in communication with the drainage lumen 16. It is contemplated that the spiral proximal portion may be pre-positioned in this state B and inserted into the urethra expanded as shown in FIG. 2. Alternatively, the proximal portion 18 may be inserted in the contracted state A and then expanded to state B in situ. This later expansion can be accomplished by advancing a stylet through the lumen 16 until it contacts the underside of the proximal tip 12. While holding the distal end of the catheter 10 outside the patient, slightly pushing the stylet will cause the spiral edges 20 to separate to state B.

In this state B one beneficial attribute may be appreciated for the present invention. In particular, the wider channels 22, as depicted in FIG. 3, may generate an auger effect to dislodge and convey an obstruction of the urethra. Thus, in one embodiment, the catheter may be rotated with the spiral proximal portion 18 in state B to initially engage an obstruction. With the obstruction lodged within the outer channel 22, the catheter may be advanced into the bladder. At this point, the catheter may be rotated clockwise so that the obstruction is augered upward into the bladder and clear of the urethra. Alternatively, the catheter may be rotated counterclockwise to propel the obstruction into the central lumen 16 where it may be flushed with urine flowing through the catheter. In this latter case, the obstruction must be much smaller than the 3 mm inner diameter of the lumen 16 of the catheter.

A third state C, illustrated in FIG. 4 is intended as a temporary measure to address problems with insertion. In this state C, the spiral proximal portion 18 is rotated relative to the distal tubular portion 14 so that the outer diameter of the distal portion is different from the fixed outer diameter of the remainder of the catheter. To accomplish the transition to state C it is necessary that the tip be restrained in some manner. Thus, the tip may engage an obstruction within the urethra to, in effect, anchor it temporarily. Alternatively, a stylet may be inserted to engage and prevent movement of the proximal tip 12 as the remainder of the catheter is rotated. As shown in FIG. 4, the spiral portion 18 can have a larger diameter in state C than the remainder of the catheter. This larger diameter may be obtained by rotating the distal-most end of the distal portion 18 counterclockwise relative to the remainder of the proximal portion. With the tip held in place, and with this counterclockwise rotation, each coil of the spiral portion expands to a larger diameter. In a specific embodiment, the state C contemplates an expanded outer diameter of 14 mm relative to the 10-11 mm diameter of the normal state A shown in FIG. 3. This enlarged diameter may be used to help open the lumen of the urethra or facilitate removal of an obstruction in the urethra.

Alternatively, the distal portion may be rotated in the clockwise direction to reduce the diameter of the proximal-most portion of the spiral portion 18. This smaller diameter may help navigate the catheter past an obstruction in the urethra. In addition, the reduced diameter in effect increases the rigidity of the spiral proximal portion which may help passage up the urethra. Again, expansion and contraction of the outer diameter can only occur if the tip is held immovable.

Transition of the spiral proximal portion 18 to the enlarged or reduced diameter of state C may be accomplished by first engaging the proximal tip 12 to hold the tip against rotation. Alternatively, a stylet having a blunt tip may thus be advanced through the catheter until it comes into frictional contact with the interior of the proximal tip. As a further alternative, the inner surface of the proximal tip may be provided with an indexing feature to be engaged by a complementary feature on the tip of the stylet. With the proximal tip 12 held against rotation, rotation of the catheter in one direction or the other will produce a commensurate change in outer diameter of the spiral proximal portion 18.

As indicated above, one beneficial feature of the present invention is that the urinary drainage catheter 10 is anchored externally, rather than internally as with the typical Foley-type catheter. In one embodiment for anchoring to a male patient, illustrated in FIG. 5, a condom catheter sheath or shroud 50 is used to anchor the endourethral catheter 10. The condom catheter shroud 50 is configured to fit over the end of the penis. The condom catheter shroud 50 includes an opening 51 that is adapted to receive an external drainage tube in a known manner. In accordance with the present invention, the condom catheter shroud is mounted on the penis with the proximal portion 14 of the drainage catheter 10 extending through the opening 51.

Figure 5:
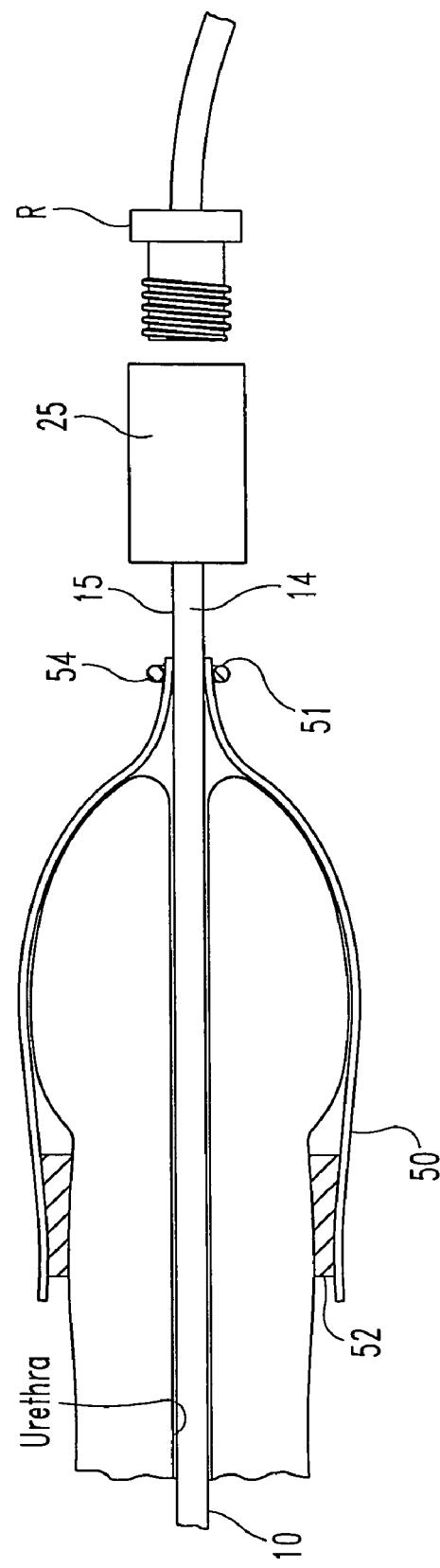
FIG. 5 is a side exterior view of a distal anchor arrangement for anchoring the catheter of the present invention within the urethra.

In one embodiment, the condom catheter shroud may engage the penis in a known manner. However, it is believed that in many cases this engagement is not sufficient to prevent movement of the drainage catheter 10 along the urethra. It is therefore contemplated in one specific embodiment that the condom catheter shroud is anchored to the skin of the shaft of the penis, such as by an adhesive strip 52. The adhesive strip is preferably configured according to the adhesive attachment disclosed in co-pending patent application Ser. No. 11/343,661, entitled "Adhesive Attachment and Removal Device", filed on Jan. 31, 2006, in the name of a common inventor to the present application. This application Ser. No. 11/343,661, the entire disclosure of which is incorporated herein by reference, discloses an double-sided adhesive strip 52 with one surface adapted for removable engagement to the skin of the penis, as shown in FIG. 5. The opposite surface is adapted to adhere to the inside of the condom catheter shroud 50, whether removable therefrom or not. The adhesive strip disclosed in this co-pending application thus provides a fluid-resistant attachment for the shroud to prevent it from sliding relative to or dislodging from the penis.

With the condom catheter thus anchored to the penis, the next aspect of the anchor system of the present invention is to anchor the drainage catheter 10 to the condom catheter shroud. In one embodiment, it is contemplated that the outer surface 15 of the drainage catheter 10 and the inner surface of the shroud 50 are formed of the same polymeric material. It is known that certain polymers, such as silicone, exhibit strong adherence between like material surfaces. Thus, in this embodiment, at least the proximal portion 14 of the catheter 10 is formed of the same material as the condom catheter shroud 50. The end of the shroud at the opening 51 may be rolled onto the outer surface 15 of the proximal portion 14 in the same way that the condom catheter shroud is rolled onto the shaft of the penis.

Alternatively, or in addition, a retention element 54 may be provided to securely fasten the condom catheter shroud around the drainage catheter. This retention element 54 may be in the form of an O-ring, strap or a circumferential clamp. It is further contemplated that other forms of attachment between the condom catheter shroud 50 and the drainage catheter 10 are contemplated, including more permanent attachment such as adhering or heat sealing the two surfaces together. Since the condom catheter shroud 50 is removably mounted to the penis, permanent attachment of the drainage catheter to the shroud does not affect the ability to remove the entire assembly from the patient.

In the present disclosed embodiments, a condom catheter shroud is used to anchor the drainage catheter 10 of the present invention to the patient. However, it is contemplated that other means for anchoring the catheter may be used. For instance, the proximal portion of the catheter may be attached to the skin of the penis, abdomen or inner thigh of the patient by medical tape.

In yet another embodiment, the endourethral catheter may be anchored externally to the female anatomy by way of an attachment to the skin of the perineum, pelvis, or inner thigh. In one embodiment, the attachment is by way of an adhesive strip utilizing the technology disclosed in the application Ser. No. 11/343,661 incorporated by reference above. The adhesive strip may be used to adhere a soft pliable shroud to adjacent available skin of a female patient, while the drainage catheter is carried by the shroud. Alternatively, the shroud may be carried on the patient by a strap arrangement.

It can be noted that attachment of the anchoring shroud, such as shroud 50, to the patient typically requires treatment of the skin surrounding the urethra with a sterilizing bath, such as povodine or betadine. Thus, when the shroud and drainage catheter are anchored to the patient, the area around the urethra has been cleansed, thereby significantly reducing the availability of bacteria to participate in the biofilm creep discussed above. In the case of the male condom catheter, once the shroud 50 is attached to the skin of the penis by the adhesive strip 52 the drainage catheter 10 is, in effect, hermetically sealed which will significantly inhibit incursion of bacteria into the urethra. Even in the case of a shroud adapted for attachment to the female anatomy, the same sterilization techniques may be observed to reduce the formation of bacteria at the site of the drainage catheter.

As shown in FIG. 5, the distal end 25 of the endourethral drainage catheter 10 provides a fitting for engaging another fitting R. In one embodiment, the two fittings are in the form of a Luer connection. It is contemplated that the mating fitting R may be connected to a urine receptacle, to a flow valve or to flow monitoring or sampling tubing.

In one embodiment of the invention, it is contemplated that the entire catheter 10 is formed from a common tube. Thus, the proximal end of the tubing may be heat molded into the tip configuration described above. The spiral proximal portion may be formed by cutting a spiral groove from the proximal tip to a predetermined distance toward the distal end of the tubing. Alternatively, the proximal tip 12 may be separately affixed to the spiral proximal portion 18 of the catheter, such as by heat sealing or adhering. In another embodiment, the distal portion 14 and the spiral proximal portion 18 may be co-extruded, or formed using a dual shot injection molding technique.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An indwelling endourethral drainage catheter comprising:
   a tubular distal portion having a distal end adapted to be situated outside the patient when the drainage catheter is indwelling, said distal portion defining a distal lumen extending along the length thereof;
   a spiral proximal portion attached to said distal portion, said proximal portion defining a proximal lumen in communication with said distal lumen and further defining a helical outer channel along the length of said spiral proximal portion, said outer channel in fluid communication with said proximal lumen; and
   an anchor assembly for anchoring the catheter within the urethra, said anchor assembly adapted to be disposed externally of the bladder and urethra, wherein said anchor assembly includes:
      a shroud configured to be disposed over the opening of the urethra of the patient;
      and an engagement between said shroud and said distal portion of the catheter arranged to be outside the urethra when the catheter is indwelling, wherein said engagement includes a clamping element encircling said shroud mounted on an outer surface of said distal portion.

2. The indwelling endourethral drainage catheter of claim 1, wherein said proximal and distal portions are integrally formed.

3. The indwelling endourethral drainage catheter of claim 1, wherein said proximal portion includes a tip at a proximal end thereof.

4. The indwelling endourethral drainage catheter of claim 1, wherein said distal end includes a fluid fitting.

5. The indwelling endourethral drainage catheter of claim 1, wherein said engagement includes a friction engagement between said shroud and the outer surface of said distal portion.

6. The indwelling endourethral drainage catheter of claim 5, wherein the friction engagement is created by said shroud and said outer surface being formed of the same polymeric material.

7. The indwelling endourethral drainage catheter of claim 1, wherein said clamping element is an O-ring.

8. The indwelling endourethral drainage catheter of claim 1, wherein said anchor assembly includes an adhesive strip adapted to be disposed between the patient's skin within said shroud and the interior of said shroud when said shroud is disposed over the opening of the urethra.

* * * * *